(12) United States Patent
Norrant et al.

(10) Patent No.: US 12,702,770 B2
(45) Date of Patent: Aug. 11, 2026

(54) DISPENSING HEAD FOR A DEVICE FOR DISPENSING A FLUID OR POWDER PRODUCT INTO THE NOSE

(71) Applicant: APTAR FRANCE SAS, Le Neubourg (FR)

(72) Inventors: Matthieu Norrant, Heudebouville (FR); Lila Graine, Beynes (FR)

(73) Assignee: APTAR FRANCE SAS, Le Neubourg (FR)

( * ) Notice: Subject to any disclaimer, the term of this patent is extended or adjusted under 35 U.S.C. 154(b) by 553 days.

(21) Appl. No.: 18/277,242

(22) PCT Filed: Feb. 14, 2022

(86) PCT No.: PCT/FR2022/050266

§ 371 (c)(1),
(2) Date: Aug. 15, 2023

(87) PCT Pub. No.: WO2022/171969

PCT Pub. Date: Aug. 18, 2022

(65) Prior Publication Data

US 2024/0139443 A1 May 2, 2024

(30) Foreign Application Priority Data

Feb. 15, 2021 (FR) ...................................... 2101439

(51) Int. Cl.
*A61M 15/08* (2006.01)
*A61M 11/00* (2006.01)
(Continued)

(52) U.S. Cl.
CPC .......... *A61M 15/08* (2013.01); *A61M 11/007* (2014.02); *A61M 15/0065* (2013.01); *B05B 11/025* (2013.01)

(58) Field of Classification Search
CPC .......... A61M 15/0028; A61M 15/0065; A61M 15/0066; A61M 15/08; A61M 11/006;
(Continued)

(56) References Cited

U.S. PATENT DOCUMENTS

2006/0254585 A1* 11/2006 Ishizeki ............ A61M 15/0043 128/203.15

FOREIGN PATENT DOCUMENTS

EP 2 976 121 B1 7/2017
FR 2 739 294 A1 4/1997
(Continued)

OTHER PUBLICATIONS

International Search Report for PCT/FR2022/050266 dated Jun. 1, 2022.

*Primary Examiner* — Joseph D. Boecker
(74) *Attorney, Agent, or Firm* — Sughrue Mion, PLLC

(57) ABSTRACT

Dispensing head for dispensing a fluid or powder product into the nose, having an axial end portion provided with a dispensing opening, the axial end portion of the head being intended to be inserted into a nostril during actuation, the head having a tip suitable for bearing on the nostril entrance during actuation so as to define the depth to which the head is inserted into the nostril, the tip being axially movable on the head between at least two use positions axially offset from each other.

8 Claims, 2 Drawing Sheets

(51) Int. Cl.
*A61M 15/00* (2006.01)
*B05B 11/02* (2023.01)

(58) Field of Classification Search
CPC ...... A61M 11/007; A61H 35/04; B05B 15/16; B05B 11/025
See application file for complete search history.

(56) References Cited

FOREIGN PATENT DOCUMENTS

| | | | | | |
|---|---|---|---|---|---|
| JP | 09-140797 | A | | 6/1997 | |
| JP | 2012135535 | A | * | 7/2012 | ............ A61M 15/08 |
| WO | 98/57690 | A1 | | 12/1998 | |
| WO | WO-0027430 | A2 | * | 5/2000 | .............. A61P 31/00 |

* cited by examiner 31
120
35
33
100
110
36
34
30
80
20
70
10
50
51
32
60
52
61

31
35
30
120
110
100
36

31
35
30
120
110
100
36

31
35
37
120
110
111
37'
36
37"
30
112
100

31
35
30
37
120
37'
110
111
37"
36
112
100

31
35
30
37
36
37'
120
37"
110
111
112
100

31
35
30
120
110
100
113
38
36
39

115

42
42'
42"
40
40'
40"
41

114
116

DISPENSING HEAD FOR A DEVICE FOR DISPENSING A FLUID OR POWDER PRODUCT INTO THE NOSE

CROSS REFERENCE TO RELATED APPLICATIONS

This application is a National Stage of International Application No. PCT/FR2022/050266 filed Feb. 14, 2022, claiming priority based on French Patent Application No. 2101439 filed Feb. 15, 2021.

The present invention relates to a dispensing head for a device for dispensing a fluid or powder product into the nose.

Devices for dispensing into the nose are broadly common and used in various applications. These devices comprise a dispensing head incorporating the opening for dispensing the product, at least one portion of said head being intended to be inserted into the nostril of the user during the dispensing of the product. The user then actuates the device for expelling a dose of product into the nostril.

In certain applications, in particular in the pharmacy field, products dispensed by devices for dispensing into the nose can be expensive and/or must be dosed very accurately. Consequently, it is sought to obtain a maximum effectiveness of the dose of product dispensed into the nostril upon each actuation.

Yet, the depth to which the dispensing head is inserted into the nostril has an effect on the dispensing of the dose. Thus, an insertion which is too deep can not only prove to be painful, but also alter the correct dispensing of the dose.

To overcome this problem, a tip has been proposed which is fixed on the dispensing head and which makes it possible, not only to limit the depth of insertion into the nostril, but also to orient, in a certain way, the dispensing head in the nostril to optimise the dispensing of the dose. Documents WO9857690 and WO0027430 describe such tips.

Yet, according to the user, the dimension of the nostril can vary quite a lot, in particular due to numerous parameters, such as the sex, the age, the size or the ethnic origin of the user.

A disadvantage of the tips of documents WO9857690 and WO0027430 resides in the fact that they do not make it possible to consider different dimensions of nostrils, and that to overcome this disadvantage, a plurality of removable tips of different sizes must be provided, the user choosing the size which suits it before use. This implementation obligates a very large number of tips to be manufactured, for example, three or four sizes for each device, while only one of these tips will actually be used.

This generates a significant manufacturing excess cost, increases the dimensions of the packaging of the device, consumes more plastic material, and therefore risks increasing environmental pollution.

Documents JP2012135535, JPH09140797, FR2739294 and EP2976121 describe other devices of the prior art.

It is an aim of the present invention, to provide a head for dispensing into the nose which does not reproduce the abovementioned disadvantages.

More specifically, it is an aim of the present invention to provide a head for dispensing into the nose which makes it possible, during actuation of the device, to define the correct depth, to which the device is inserted into the nostril, suitable for each user.

It is also an aim of the present invention to provide a head for dispensing into the nose of the abovementioned type, which is simple and inexpensive to manufacture and to assemble.

It is also an aim of the present invention to provide such a head for dispensing into the nose which is simple and reliable to use for any user.

The present invention therefore aims for a head for dispensing a fluid or powder product into the nose, comprising an axial end portion provided with a dispensing opening, said axial end portion of said head being intended to be inserted into the nostril during actuation, said head comprising a tip, suitable for bearing on the nostril entrance during actuation to define the depth to which said head is inserted into the nostril, said tip being axially movable on said head between at least two positions of use axially offset from each other, said tip comprising a hollow cylindrical axial sleeve disposed around a cylindrical portion of said head, said sleeve extending from the upper axial side by a radial flange which extends radially outwards, said radial flange bearing on the nose around the nostril entrance during actuation, said cylindrical portion comprising at least two external radial recesses axially offset, and at least one flat spot axially extending in said cylindrical portion, each flat spot comprising at least two ribs extending radially outwards, each rib being disposed at a respective external radial recess, said sleeve comprising at least one internal radial projection, the internal diameter of said sleeve at said at least one internal radial projection being greater than the external diameter of the cylindrical portion at said at least one flat spot, almost identical to the external diameter of the cylindrical portion at each rib and less than the external diameter of the cylindrical portion of each external radial recess, such that said tip can axially slide on said head when said at least one internal radial projection is disposed at a flat spot and said tip cannot axially slide on said head when said at least one internal radial projection is disposed in an external radial recess, after rotation of said tip on said head, said at least one internal radial projection being disposed in a first radial recess in a first position of use and in a second radial recess in a second position of use.

Advantageously, said cylindrical portion comprises two diametrically opposite flat spots, three external radial recesses and three ribs, each external radial recess extending over the periphery of said cylindrical portion by being interrupted at each flat spot, and each rib extending over each of said two flat spots.

Advantageously, said sleeve comprises two diametrically opposite internal radial projections.

Advantageously, said radial flange has a radially external edge with a rounded shape, in particular, circular or oval.

The present invention also aims for a device for dispensing fluid product, comprising a reservoir and a dispensing member, such as a piston, slidingly mounted in said reservoir, said device comprising a dispensing head such as described above.

Advantageously, said reservoir contains one single dose of fluid product dispensed in one single actuation.

Advantageously, said reservoir contains two doses of fluid product dispensed in two successive actuations.

These features and advantages and others of the present invention will appear more clearly in the detailed description below given as a non-limiting example in reference to the accompanying drawings, wherein:

FIG. 1 is a schematic, cross-sectional view of a device for dispensing fluid product into the nose, in the rest position, FIGS. 2 and 3 are schematic, detailed, cross-sectional views, showing the tip according to a first embodiment, in two different positions of use, FIGS. 4 to 6 are schematic, detailed, cross-sectional views, showing the tip according to a second embodiment, in three different positions of use, FIGS. 7 to 9 are schematic, detailed, side views, showing the tip according to a third embodiment, in three different positions of use, FIGS. 10 to 12 are schematic, detailed, cross-sectional views, showing the tip of the third embodiment in its three different positions of use, FIG. 13 is a schematic, detailed, perspective view, showing the dispensing head according to a fourth embodiment, FIG. 14 is a schematic, detailed, perspective view, showing the tip of the fourth embodiment, FIG. 15 is a schematic, detailed, perspective view, showing the tip of the fourth embodiment engaging with the dispensing head, and FIGS. 16 to 18 are schematic, detailed, cross-sectional views, showing the tip of the fourth embodiment in three different positions of use.

In the description below, the terms “axial” and “radial” refer to the longitudinal central axis of the device. The terms “upper”, “lower”, “top” and “bottom” refer to the straight position of the device represented in FIG. 1.

The present invention is described below with reference to a dual-dose embodiment, i.e. a device containing two doses of fluid product to be dispensed during two successive actuations of the device. It is, however, understood that the present invention could be applied to devices comprising one single dose or a greater number of doses, for example three or four doses. Likewise, the dual-dose-type device represented in the drawings is only one possible example of an embodiment to which the present invention applies, and it is understood that the present invention applies more generally to any type of device containing at least one dose.

With reference to FIG. 1, the device for dispensing into the nose comprises a reservoir 10 containing two doses of fluid product. A dispensing member, such as a piston 20, is slidingly mounted in said reservoir 10. In the position before the actuation of the device, represented in FIG. 1, said piston 20 acts as a stopper by isolating the content of the reservoir 10.

A dispensing head 30 is assembled on said reservoir 10, being axially movable with respect to it. In particular, an axial movement of the dispensing head 30 with respect to the reservoir 10 causes the piston 20 to move in the reservoir 10, and thus causes the fluid product contained in said reservoir to be dispensed. The dispensing head 30 comprises a dispensing channel 33 which leads from a piercing tip 34 to a dispensing opening 31 of the dispensing head 30. Upstream from the dispensing opening 31, a spraying profile can be provided, which can be of any known type and which is not represented in more detail in the drawing, to dispense the fluid product in spray form.

More specifically, in the example represented, the reservoir 10 is fixed in a body 50, which is therefore integral with said reservoir 10, and which is moved together with it.

The dispensing head 30 comprises a lower side skirt 32 suitable to engage with an actuation member 60. A finger-rest element 80 is formed integrally with said dispensing head 30, or in a variant, is assembled around it.

Said actuation member 60 is axially movable inside said side skirt 32 of the dispensing head 30 to perform successive device actuations. The actuation member 60 comprises at least one inclined tab 61 which is suitable for engaging with projections 51, 52 of the body 50 to perform successive actuations.

A return spring 70 is mounted between the actuation member 60 and the dispensing head 30, to return said actuation member 60 in its starting position after each actuation.

The operation of the device represented in FIG. 1 is as follows. In the rest position of FIG. 1, the stopper piston 20 isolates the content of the reservoir 10 from the atmosphere. When the user simultaneously presses on the finger-rest 80 and on the actuation member 60, it will move said actuation member 60 inside the side skirt 32 of the dispensing head 30. This will push the body 50 axially upwards, by way of the tabs 61 which will push on the shoulder 51 of said body. This will compress the spring 70 and move the reservoir 10 with respect to the dispensing head 30. When the reservoir 10 will start to move with respect to the dispensing head 30, the piercing end 34 of the dispensing channel 33 will pierce the stopper piston 20 to make the inside of the reservoir 10 communicate with said expulsion channel 33. A continuation of the actuation will cause a movement of the piston 20 inside the reservoir and therefore a dispensing of the first dose. The fluid product is therefore pushed by said piston 20 through the piercing end 34 into the dispensing channel 33, then outside of the device through the dispensing opening 31.

After the dispensing of the first dose, when the user releases the actuation member 60, the spring 70 will return it to its starting position. During this return of the actuation member 60, the reservoir and the body 50 do not move back, as these two components remain held in said dispensing head 30. Optionally, the dispensing head 30 can comprise non-return means, so as to prevent said body 50 and/or said reservoir 10 from moving back. When the actuation member 60 returns under the effect of the return spring 70 to its rest position, the tabs 61 will be positioned under the second projection 52 of the body 50 which will make it possible for the user to actuate, for a second time, the device for dispensing the second dose of fluid product.

The dispensing device can comprise an indicator (not represented) to indicate to the user, the dispensing of the first dose and the dispensing of the second dose. In this way, the user exactly knows the situation and whether the first dose has been dispensed or not. This indicator can comprise a viewing window formed in said dispensing head 30.

The device for dispensing into the nose comprises a tip 100 which is disposed on the head 30 to define the depth to which the dispensing head is inserted into the nostril.

Advantageously, the tip 100 comprises a hollow cylindrical axial sleeve 110 disposed around a cylindrical portion 36 of said head 30, said axial sleeve 110 ending on the upper axis side by a radial flange 120 which extends radially outwards. This radial flange 120 of the tip 100 comes to bear on the nose, around the nostril, to define the depth to which the head 30 is inserted into the nostril.

The radially external edge of the radial flange 120 is advantageously rounded-shaped, for example circular as represented in FIGS. 14 and 15, but any other shape can be considered, for example an oval shape.

By its radial dimension, the radial flange 120 also makes it possible to orient in a certain way, the head 30 in the nostril, with, in particular, the radially external edge of said radial flange 120 which can come to bear on the upper lip, under the nostril, as described in document WO9857690.

According to the invention, the tip 100 is adjustable before each use of the device, i.e. that it is axially movable on the head 30 between at least two positions of use axially offset from each other. The figures show three different embodiments, with two or three different positions of use, but it is understood that any number of different positions can be considered.

FIGS. 2 and 3 illustrate a first embodiment.

In this first embodiment, the sleeve 110 of the tip 100 is force fitted on the cylindrical portion 36 of said head 30.

The force necessary to axially move the tip 100 on the head 30 between its positions of use is greater than the bearing force of said tip 100 on the nose during actuation. Thus, there is no risk that the tip moves on the head during actuation.

Figures 1, 2, 3, 4, 5, 6:
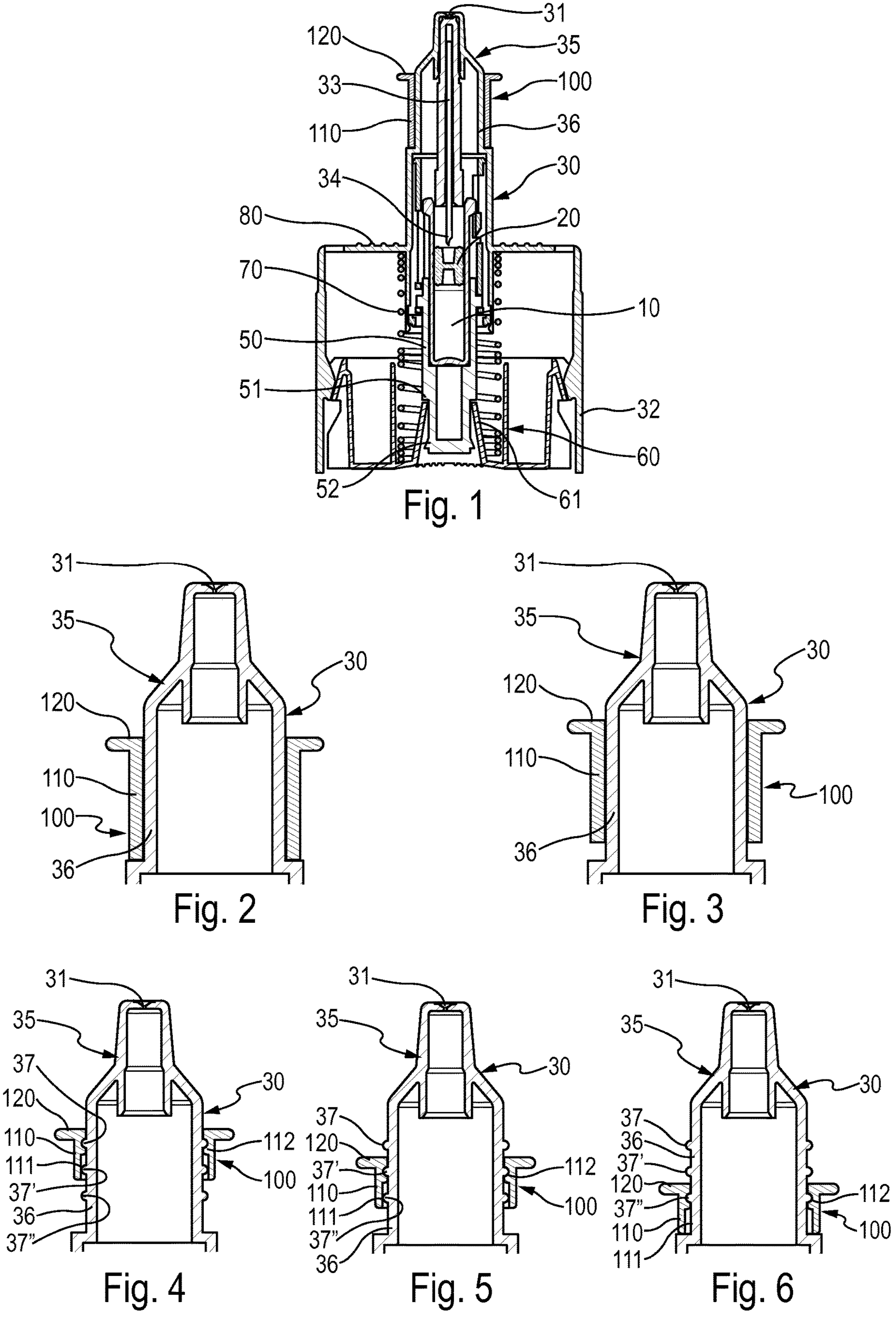
FIG. 2 shows a first position of use of the tip, wherein the tip 100 is in a lower position, therefore with a larger portion of the head which will enter into the nostril during actuation.
FIG. 3 shows a second position of use of the tip, wherein the tip 100 is in an upper position, axially offset upwards with respect to the first lower position of FIG. 2, therefore with a smaller portion of the head which will enter into the nostril during actuation.

FIGS. 4 to 6 illustrate a second embodiment.

In this second embodiment, the cylindrical portion 36 comprises at least two axially offset external radial projections 37; 37'; 37" and the sleeve 110 comprises at least one internal radial recess 112.

The internal radial recess 112 engages, in particular by snap-fitting, with a first radial projection 37 in a first position of use, which is an upper position of use, represented in FIG. 4.

In a second intermediate position of use, which can be seen in FIG. 5, the internal radial recess 112 engages with a second radial projection 37', and in a third position of use, which is a lower position of use which can be seen in FIG. 6, it engages with a third radial projection 37".

In a variant, the radial projections of the head could be replaced with recesses, and the recess of the tip with a projection.

Advantageously, the tip 100 comprises a peripheral internal radial recess 112. This makes it possible to not have to orient the tip angularly with respect to the head.

In the example represented, the radial recess 112 is disposed in the proximity of the radial flange 120, and the sleeve 110 thus advantageously comprises a cutout 111, preferably peripheral, on its lower portion to receive the radial projection(s) disposed below the radial projection which engages with the radial recess 112.

Advantageously, each external radial projection 37; 37'; 37" is peripheral, forming a beading all around the head. In a variant, one or more projecting lugs could be provided, instead of a peripheral bead.

FIGS. 7 to 12 illustrate a third embodiment.

In this third embodiment, the cylindrical portion 36 comprises an external threading 38 and the sleeve 110 comprises an internal threading 115 engaging with said external threading 38, the tip 100 being rotatably movable on the head 30 between its positions of use.

Advantageously, the friction between said internal and external threadings 115, 38 prevents a rotation of said tip 100 during actuation. In other words, there is no risk that the tip moves on the head during actuation.

In the example represented in the figures, the external threading 38 is a female threading, i.e. that the thread is hollowed in the cylindrical portion 36 and the internal threading 115 is a male threading, i.e. that the thread projects radially inwards from said sleeve 110. Naturally, the opposite implementation is also possible.

Figures 7, 8, 9, 10, 11, 12, 13, 14, 15, 16, 17, 18:
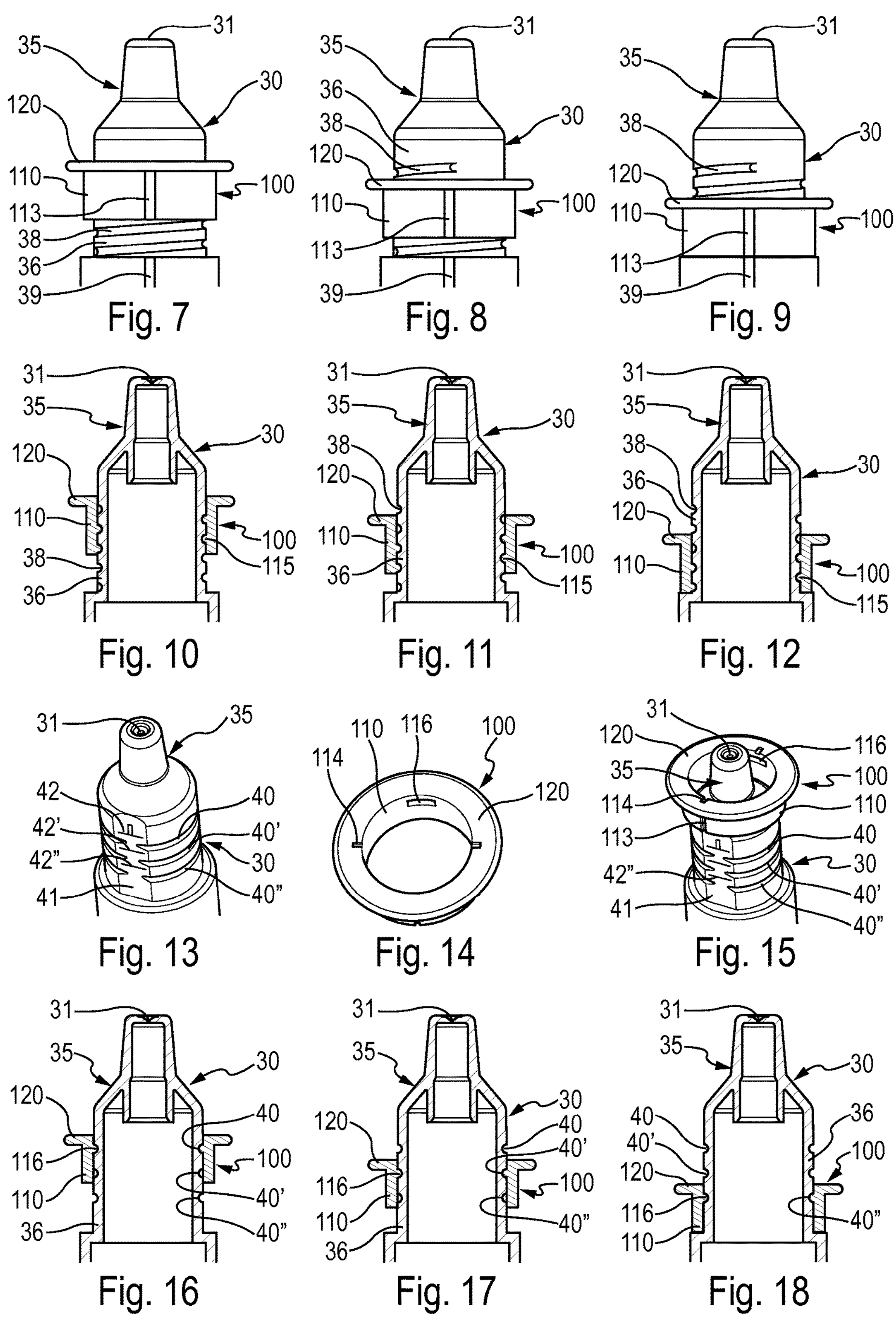

Advantageously, three positions of use are defined, namely an upper position, represented in FIGS. 7 and 10, an intermediate position, represented in FIGS. 8 and 11, and a lower position, represented in FIGS. 9 and 12. A marker 113 can thus advantageously be provided on the outside of the sleeve 110 of the tip 100, and a corresponding marker 39 on the head 30, in particular on a portion of the head 30 disposed below the tip 100. As can be seen in FIGS. 7 to 9, the correspondence of the marker 113 of the tip with the marker 39 of the head defines the respective position of use. Optionally, resistance points can be provided on the external threading 38 and/or the internal threading 115 (not represented) to define these different positions of use of the tip.

FIGS. 13 to 18 illustrate a fourth embodiment according to the invention.

In this fourth embodiment, the cylindrical portion 36 comprises at least two axially offset external radial recesses 40; 40'; 40".

At least one flat spot 41 extends axially into said cylindrical portion 36. Advantageously, two diametrically opposite flat spots are provided.

Each flat spot 41 comprises at least two ribs 42; 42'; 42" extending radially outwards, each rib 42; 42'; 42" being disposed at a respective external radial recess 40; 40'; 40". Advantageously, three external radial recesses 40; 40'; 40" and three ribs 42; 42'; 42" are provided, each external radial recess 40; 40'; 40" extending over the periphery of the cylindrical portion 36 by being interrupted at each flat spot 41, and each rib 42; 42'; 42" extending over each of the flat spots 41.

The sleeve 110 comprises at least one internal radial projection 116. Advantageously, the sleeve 110 comprises two diametrically opposite internal radial projections 116.

The internal diameter of said sleeve 110 at the internal radial projections 116 is greater than the external diameter of the cylindrical portion 36 at said at least one flat spot 41, almost identical to the external diameter of the cylindrical portion 36 at each rib 42; 42'; 42", and less than the external diameter of the cylindrical portion 36 at each external radial recess 40; 40'; 40". Thus, the tip 100 can axially slide on the head 30 when each internal radial projection 116 is disposed at a respective flat spot 41 and the tip 100 cannot axially slide on the head 30 when each internal radial projection 116 is disposed in a respective external radial recess 40; 40'; 40", after rotation of the tip 100 on the head 30.

In the example represented, where the head comprises three external radial recesses 40; 40'; 40" and three ribs 42; 42'; 42", three positions of use are defined, namely an upper position, represented in FIG. 16, an intermediate position, represented in FIG. 17, and a lower position, represented in FIG. 18.

In the upper position of use, each internal radial projection 116 is disposed in a first respective radial recess 40. In the intermediate position of use, each internal radial projection 116 is disposed in a second respective radial recess 40'. In the lower position of use, each internal radial projection 116 is disposed in a third respective radial recess 40".

The ribs 42; 42'; 42" serve to easily identify each of the axial positions of the tip. Indeed, by their excess thickness with respect to the flat spot 41, they engage with the internal radial projection(s) 116 to form a resistance to the axial sliding of the tip 100. Thus, these ribs do not prevent this sliding, but each rib makes it possible to accurately identify the axial position of each respective radial recess 40, 40', 40". Thus, the user who wants to go from the upper position to the intermediate position, rotates the tip 100 such that each internal radial projection 116 faces a respective flat spot

41 and presses on the tip to move it axially downwards. When the internal radial projection reaches the rib 42' of the intermediate position, the axial movement of the tip is stopped, and the user can thus rotate the tip with respect to the head to bring each radial projection 116 into a respective radial recess 40'. If, however, the user wants to go to the lower position, they press harder on the tip to overcome the resistance generated by the rib 42', and they can thus axially move the tip further downwards.

Advantageously, the tip 100 comprises a marker 113 on the sleeve 110, disposed at each internal radial projection 116. Optionally, a second marker 114 can also be provided on the radial flange 120, also disposed at each internal radial projection 116. This makes it possible to guide the user to easily identify the angular position in which they can move the tip axially with respect to the head, by aligning the marker(s) 113, 114 with a flat spot 41.

Other variants of embodiment can be designed to perform the function claimed by the present invention.

The operation of the device is as follows.

Before use, the user adjusts the position of use of the tip 100 on the axial end of the head 30. They thus insert the head 30, at least its axial end, into their nostril. During this operation, the radial flange 120 of the tip 100 comes to bear on the nose wing, to define the depth said head 30 is inserted into the nostril. The user thus actuates the device and the dose of the product is dispensed into the nostril.

The present invention therefore makes it possible to provide a head for dispensing into the nose which is simple and inexpensive to manufacture (in particular, to mould) and to assemble. This head is furthermore simple and reliable to use by everyone. This is particularly advantageous in the pharmacy field where the dosing of the product must be very accurate and its effectiveness optimised due to the often high cost of the products to be dispensed.

The present invention has been described in reference to several particular embodiments of it, but it is clear that various modifications are possible, without moving away from the scope of the present invention such as defined by the accompanying claims.

The invention claimed is:

1. A head for dispensing a fluid or powder product into a nose, comprising an axial end portion provided with a dispensing opening, said axial end portion of said head being intended to be inserted into a nostril during actuation, said head comprising a tip suitable for bearing on the nostril entrance during actuation, to define the depth to which said head is inserted into the nostril, said tip being axially movable on said head between at least two positions of use axially offset from each other, said tip comprising a hollow cylindrical axial sleeve disposed around a cylindrical portion of said head, said sleeve extending from an upper axial side by a radial flange which extends radially outwards, said radial flange bearing on the nose around the nostril entrance during actuation, wherein said cylindrical portion comprises at least two axially offset external radial recesses, and at least one flat spot extending axially into said cylindrical portion, each flat spot comprising at least two ribs extending radially outwards, each rib being disposed at a respective external radial recess, said sleeve comprising at least one internal radial projection, the internal diameter of said sleeve at said at least one internal radial projection being greater than the external diameter of the cylindrical portion at said at least one flat spot, almost identical to the external diameter of the cylindrical portion at each rib and less than the external diameter of the cylindrical portion at each external radial recess, such that said tip can axially slide on said head when said at least one internal radial projection is disposed at a flat spot and said tip cannot axially slide on said head when said at least one internal radial projection is disposed in an external radial recess, after rotation of said tip on said head, said at least one internal radial projection being disposed in a first radial recess in a first position of use and in a second radial recess in a second position of use.

2. The head according to claim 1, wherein said cylindrical portion comprises two diametrically opposite flat spots, three external radial recesses and three ribs, each external radial recess extending over the periphery of said cylindrical portion by being interrupted at each flat spot, and each rib extending over each of said two flat spots.

3. The head according to claim 1, wherein said sleeve comprises two diametrically opposite internal radial projections.

4. The head according to claim 1, wherein said radial flange has a radially external edge with a rounded-shape, in particular circular or oval.

5. A device for dispensing fluid product, comprising a reservoir and a dispensing member, slidingly mounted in said reservoir, wherein said device comprises a dispensing head according to claim 1.

6. The device according to claim 5, wherein said reservoir contains one single dose of fluid product dispensed in one single actuation.

7. The device according to claim 5, wherein said reservoir contains two doses of fluid product dispensed in two successive actuations.

8. The device according to claim 5, wherein the dispensing member is a piston.

* * * * *